US00PP25176P3

(12) United States Plant Patent
Nishimoto

(10) Patent No.: US PP25,176 P3
(45) Date of Patent: Dec. 16, 2014

(54) *BEGONIA* PLANT NAMED 'BGDCR21-0'

(50) Latin Name: *Begonia semperflorens*
Varietal Denomination: BGDCR21-0

(71) Applicant: Shinichi Nishimoto, Fukuoka (JP)

(72) Inventor: Shinichi Nishimoto, Fukuoka (JP)

(73) Assignee: Suntory Flowers Ltd (JP)

( * ) Notice: Subject to any disclaimer, the term of this patent is extended or adjusted under 35 U.S.C. 154(b) by 198 days.

(21) Appl. No.: 13/694,344

(22) Filed: Nov. 20, 2012

(65) Prior Publication Data

US 2014/0143921 P1 May 22, 2014

(51) Int. Cl.
*A01H 5/00* (2006.01)

(52) U.S. Cl.
USPC ..... Plt./349

(58) Field of Classification Search
USPC ..... Plt./349
See application file for complete search history.

*Primary Examiner* — Annette Para
(74) *Attorney, Agent, or Firm* — Cassandra Bright

(57) ABSTRACT

A new and distinct *Begonia semperflorens* cultivar named 'BGDCR21-0' is disclosed, characterized by, double red flowers, and bronze leaves, uniform plant shapes that branch easily and plants that flower early. The new variety is a *Begonia*, and is normally used as an ornamental garden or container plant.

1 Drawing Sheet

Latin name of the genus and species: *Begonia semperflorens.*

Variety denomination: 'BGDCR21-0'.

BACKGROUND OF THE INVENTION

The new cultivar is the product of a planned breeding program. The new variety originated as the result of a crossing performed in October of 2007 of an unnamed, unpatented proprietary seed parent variety of *Begonia semperflorens* with the pollen parent, an unnamed, unpatented proprietary variety of *Begonia semperflorens*. The new variety was discovered by the inventor, Shinichi Nishimoto, a citizen of Japan, at a research greenhouse in Yama, Fukuoka, Japan, in September of 2008.

Asexual reproduction of the new cultivar 'BGDCR21-0' was first performed in Yama, Fukuoka, Japan in June 2009. 'BGDCR21-0' has since produced several generations by vegetative cuttings and has shown that the unique features of this cultivar are stable and reproduced true to type.

SUMMARY OF THE INVENTION

The cultivar 'BGDCR21-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BGDCR21-0.' These characteristics in combination distinguish 'BGDCR21-0' as a new and distinct *Begonia semperflorens* cultivar:

1. Double flower.
2. Bronze leaf color.
3. Red flower color.
4. Easy branching.
5. Early flowering.
6. Compact, regular plant shape.

PARENT COMPARISON

Plants of the new cultivar 'BGDCR21-0' are similar to plants of the seed parent variety in most horticultural characteristics. However, plants of the new cultivar 'BGDCR21-0' produce a double flower, compared to the single flower of the seed parent. Additionally, plants of the new variety grow faster, and are taller and wider than plants of the seed parent.

Plants of the new cultivar 'BGDCR21-0' are similar to plants of the pollen parent variety in most horticultural characteristics. However, plants of the new cultivar 'BGDCR21-0' produce different colored flowers, and different colored foliage. Additionally, plants of the new variety are more uniform and compact in shape than the pollen parent.

COMMERCIAL COMPARISON

Plants of the new cultivar 'BGDCR21-0' are similar to plants of the commercial variety, *Begonia semperflorens* 'Doublet Red' U.S. Plant Pat. No. 12,638, in most horticultural characteristics. However, plants of the new cultivar 'BGDCR21-0' are taller and have a more uniform growth habit. Plants of the new cultivar are also more tolerant of common fungal diseases of *Begonia semperflorens* than 'Doublet Red'.

BRIEF DESCRIPTION OF THE PHOTOGRAPH

The aforementioned photograph and following observations and measurements describe plants grown in Oxnard, Calif. under commercial practice during the summer and fall in a greenhouse with day temperatures about 21° to 27° C., night temperatures about 16° to 18° C. and light levels about 4,000 to 8,000 foot-candles. Unrooted cuttings were directly planted in 6 inch containers and grown for about eight weeks.

The accompanying photograph in FIG. 1 illustrates in full color a typical plant of 'BGDCR21-0' grown in a greenhouse. The pot size is a commercial 6 inch pot. The plant shown is approximately 8 weeks old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'BGDCR21-0' plants grown in a commercial controlled greenhouse in Oxnard, Calif. Measurements and numerical values represent averages of typical plant types.

Botanical classification: *Begonia semperflorens* 'BGDCR21-0'.

Age of plant described: Approximately 8 weeks.

Container size of plant described: 6 inch pot.

PROPAGATION

Type of propagation typically used: Vegetative tip cuttings.

Time to develop roots: About 15 to 20 days at approximately 20° C.

Root description: Fibrous, fleshy, fine.

PLANT

Growth habit: Compact, upright and uniform plant habit; mounded inverted triangle.

Pot size of plant described: 6 inch.

Height: 13 cm.

Plant spread: 22 cm.

Growth rate: Low to moderate.

Branching characteristics: Moderately well branched, approximately 3 breaks from a pinch.

Length of primary lateral branches: 8 cm.

Quantity of primary lateral branches: About 10.

Characteristics of primary lateral branches:

- *Form*.—Round in cross section.
- *Diameter*.—Approximately 0.6 cm.
- *Color*.—Near RHS Yellow-Green 146C, flushed Greyed-Purple 184B.
- *Texture*.—Glabrous, shiny.
- *Strength*.—Moderately strong and flexible.

Internode length: 3.5 cm.

FOLIAGE

- *Arrangement*.—Alternate.
- *Quantity*.—Approximately 6 to 8 per primary lateral branch.
- *Average length*.—Approximately 6.0 cm.
- *Average width*.—Approximately 6.0 cm.
- *Shape of blade*.—Orbicular.
- *Apex*.—Broadly acute.
- *Base*.—Cordate.
- *Margin*.—Very slightly scalloped.
- *Texture of top surface*.—Glabrous.
- *Texture of bottom surface*.—Glabrous.
- *Pubescence*.—None.
- *Aspect*.—Strong upward curve to overall leaf, margins slightly curled under.
- *Color*.—Young foliage upper side: Near RHS Brown 200B. Young foliage under side: Near RHS Greyed-Orange 166A, strong coloration along veins, Yellow-Green 144B. Mature foliage upper side: Near RHS Greyed-Purple 187A. Mature foliage under side: Near RHS Greyed-Red 178A.
- *Venation*.—Type: Palmate. Venation color upper side: Near RHS Yellow-Green 144B. Venation color under side: Near RHS Yellow-Green 144B.
- *Petiole*.—Length: Approximately 0.9 cm. Diameter: Approximately 0.4 cm. Color: Near RHS Yellow-Green 151C, strong flush near Greyed-Red 180A. Texture: Glabrous.
- *Stipule description*.—Approximately 2 per node, non-fleshy, becoming completely papery before leaves fully expand. Length: Approximately 0.8 cm. Diameter: Approximately 0.4 cm. Color: Near RHS Yellow-Green 144B. Texture: Glabrous.

FLOWER

Flowering habit: Continuously flowering during Spring and Summer.

Inflorescence and flower type and habit: Double flowers with numerous tepals arranged in axillary cymes. Cymes held above foliage, approximately 3 to 5 flowers per cyme.

Cyme size:

- *Diameter*.—Approximately 7 cm.
- *Height*.—Approximately 3.5 cm.

Flower longevity on plant: About 10 days.

Persistent or self-cleaning: Self-Cleaning.

Bud:

- *Shape*.—Orbicular.
- *Length*.—Approximately 1.2 cm.
- *Diameter*.—Approximately 1.5 cm.
- *Color*.—Near RHS Red 53B.

Flower size:

- *Diameter*.—Approximately 2.2 cm.
- *Depth*.—Approximately 1.5 cm.

Tepals:

- *Quantity*.—Approximately 50.
- *Arrangement*.—Rosette.
- *Length*.—Approximately 0.8 cm.
- *Width*.—Approximately 0.6 cm.
- *Shape*.—Obovate.
- *Apex*.—Obtuse.
- *Base*.—Rounded.
- *Margin*.—Entire.
- *Aspect*.—Slight upward curve.
- *Texture, upper and lower surfaces*.—Matte.
- *Color*.—When opening, upper surface: Near RHS Red 53A. When opening, lower surface: Near RHS Red 53A. Fully opened, upper surface: Near RHS Red 53B. Fully opened, lower surface: Near RHS Red 53B.

Flower bracts:

- *Quantity per flower*.—2.
- *Shape*.—Reniform.
- *Length*.—Approximately 1.5 cm.
- *Diameter*.—Approximately 1.1 cm.
- *Apex*.—Obtuse.
- *Margin*.—Entire.
- *Texture*.—Glabrous.
- *Aspect*.—Strongly curved inward towards tepals.
- *Color*.—Near RHS Red 53C.

Peduncles:

- *Length*.—Average 3.0 cm.
- *Diameter*.—Approximately 0.2 cm.

*Angle*.—About 15° to the lateral branch.
*Strength*.—Moderate, flexible.
*Texture*.—Glabrous, shiny.
*Color*.—Near RHS Greyed-Purple 184C.

Pedicels:
*Length*.—Approximately 1.2 cm.
*Diameter*.—Approximately 0.1 cm.
*Angle*.—About 15° to the lateral branch.
*Strength*.—Moderate, flexible.
*Texture*.—Glabrous, shiny.
*Color*.—One side near Red 46A, other side near Red 48B.

Fragrance: None.

REPRODUCTIVE ORGANS

Reproductive organs are not present on the double flowers. Infrequently, 1 or 2 single flowers occur on a plant. The following describes the reproductive organs found on these single flowers.

Stamens:
*Number*.—8.

Anthers:
*Description*.—Fleshy, undulating, linear.
*Length*.—Approximately 0.2 cm.
*Color*.—Near RHS Yellow 9B.
*Pollen*.—Not observed.

Pistil:
*Number*.—1.
*Length*.—Approximately 0.8 cm.
*Style*.—Length: Approximately 0.2 cm. Color: Near RHS Yellow-Green 145B.
*Stigma*.—Shape: Linear. Color: Near RHS Yellow-Green 145D. Ovary Color: Near RHS Yellow-Green 145B.

OTHER CHARACTERISTICS

Seeds and fruits: Not observed to date.

Disease/pest resistance: Neither resistance nor susceptibility to diseases or pests has been observed in this variety.

Temperature tolerance: The new variety tolerates temperatures from approximately 5° to 35° C.

What is claimed is:

1. A new and distinct cultivar of *Begonia* plant named 'BGDCR21-0' as herein illustrated and described.

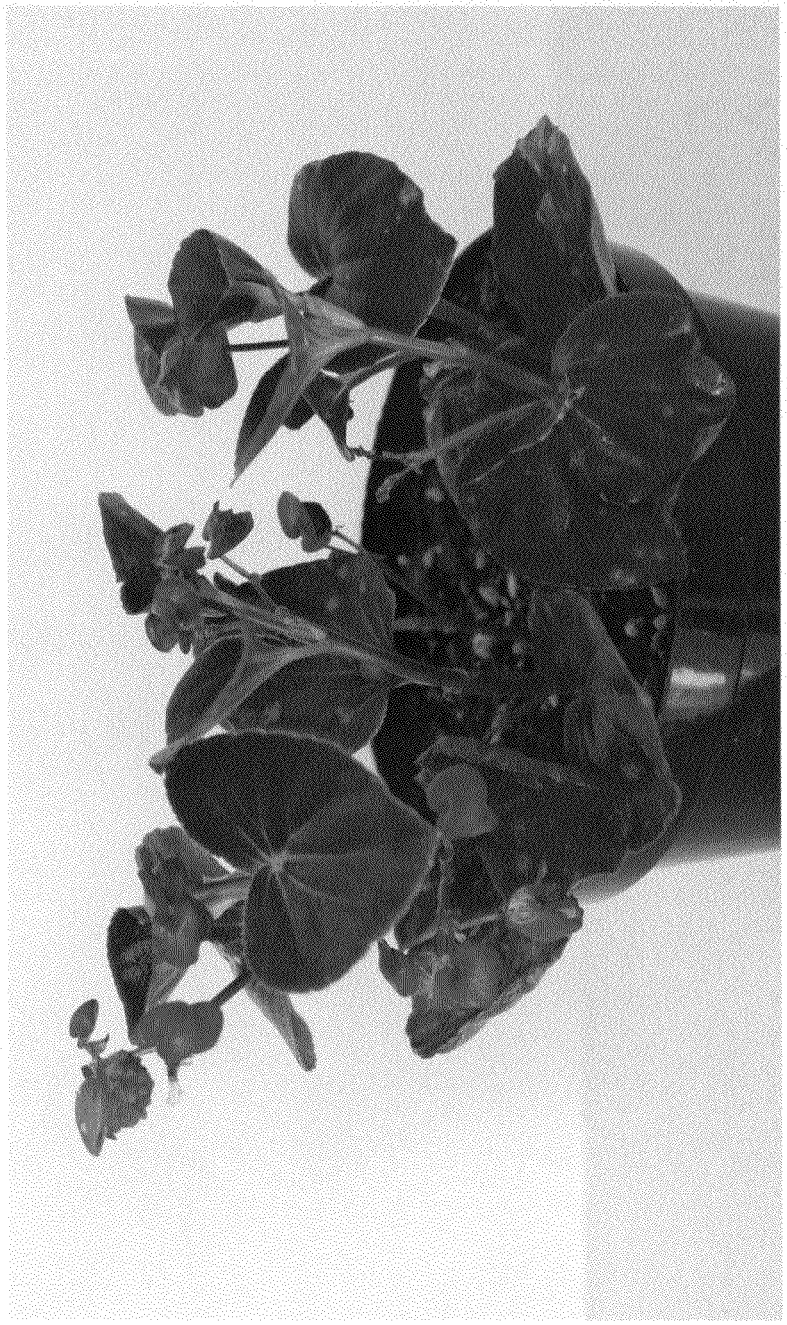

* * * * *